(12) United States Patent
Candau et al.

(10) Patent No.: US 6,558,655 B2
(45) Date of Patent: *May 6, 2003

(54) ARTIFICIAL TANNING COMPOSITIONS COMPRISING FLAVYLIUM SALTS

(75) Inventors: Didier Candau, Bievres (FR); Serge Forestier, Claye Souilly (FR)

(73) Assignee: Société l'Oréal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/902,628

(22) Filed: Jul. 12, 2001

(65) Prior Publication Data

US 2002/0048555 A1 Apr. 25, 2002

(30) Foreign Application Priority Data

Jul. 12, 2000 (FR) .............................. 00 09108

(51) Int. Cl.⁷ .............................. A61K 7/42; A61K 7/44; A61K 7/00
(52) U.S. Cl. .......................... 424/59; 424/60; 424/400; 424/401
(58) Field of Search ........................... 424/59, 60, 400, 424/401

(56) References Cited

FOREIGN PATENT DOCUMENTS

| CN | 1209992 | 3/1999 |
|---|---|---|
| FR | 2 757 383 A1 | 6/1998 |
| FR | 2 757 383 | 6/1998 |
| HU | 195 618 B | 8/1984 |
| HU | 205 554 A | 5/1992 |
| JP | 63 135310 A | 6/1988 |
| JP | 63-135310 | 6/1988 |
| RU | 2 128 990 C | 4/1999 |

OTHER PUBLICATIONS

Search Report Issued in French Priority Application No. 00/09108, Dated Apr. 26, 2001, 3 Pages.

*Primary Examiner*—Shelley A. Dodson
(74) *Attorney, Agent, or Firm*—Finnegan, Henderson, Farabow, Garrett & Dunner, L.L.P.

(57) ABSTRACT

Topically applicable cosmetic/dermatological compositions for artificially tanning/darkening human skin to such extent as to resemble a natural tan, comprise a thus effective amount of at least one flavylium salt compound formulated into a topically applicable, cosmetically/dermatologically acceptable vehicle, diluent or carrier therefor, the at least one flavylium salt compound being unsubstituted at position-3 thereof, but otherwise substituted with at least one hydroxyl group or alkoxy radical; characteristically the amount of the at least one flavylium salt compound is such as to impart a skin coloration, within about 30 minutes after application onto a fair skin, at a rate of 2 mg/cm$^2$, having a $\Delta L^*$ ranging from −0.5 to −20 in the $L^*a^*b^*$ colorimetric measuring system.

26 Claims, No Drawings

ARTIFICIAL TANNING COMPOSITIONS COMPRISING FLAVYLIUM SALTS

CROSS-REFERENCE TO PRIORITY APPLICATION

This application claims priority under 35 U.S.C. §119 of FR-00/09108, filed Jul. 12, 2000, hereby expressly incorporated by reference.

BACKGROUND OF THE INVENTION

1. Technical Field of the Invention

The present invention relates to novel cosmetic and/or dermatological compositions comprising at least one flavylium salt compound which is unsubstituted at position-3 thereof, but which is otherwise substituted with at least one hydroxyl or alkoxy radical, for imparting to human skin an artificial coloration similar to that of a natural tan.

2. Description of the Prior Art

Today, it is important to look healthy and a tanned skin is always a sign of good health. However, a natural tan is not always desirable since it requires long exposure to UV radiation, in particular to UV-A radiation which causes the tanning of the skin but, in contrast, is liable to induce an adverse change therein, in particular in the case of sensitive skin or of skin which is continually exposed to solar radiation. It is thus desirable to find an alternative to a natural tan which is compatible with the requirements of such skin types.

Most of the cosmetic products intended for artificially tanning the skin are based on carbonyl compounds which, by interacting with the amino acids in the skin, form colored species.

To this end, it is known that dihydroxyacetone, or DHA, is a particularly advantageous product which is commonly formulated into cosmetics as an agent for artificially tanning/browning the skin; when applied to the skin, in particular to the face, it provides a tanning or bronzing effect which is similar in appearance to that which may result from prolonged exposure to sunlight (a natural tan) or under a UV lamp.

The disadvantage and drawback of DHA is the length of time required for the coloration to develop: specifically, several hours (3 to 5 hours in general) are required for the coloration to be revealed. There is, thus, an increasing demand for fast-acting self-tanning products which impart a coloration closer to that of a natural tan.

Considerable research is ongoing to develop novel compounds and novel compositions for imparting to the skin an artificial coloration close to that of a natural tan in a simple, effective, fast and risk-free manner.

Anthocyanin colorants have long been known as pharmaceutical and food colorants. These anthocyans are present in nature in the form of heterosides known as anthocyanosides and genins, known as anthocyanidines. These anthocyans are phenyl-2-benzopyrylium or flavylium derivatives and are present, in particular, in the plant in the form of salts. Anthocyans are red-, violet- or blue-colored compounds which generally color flowers, fruit and occasionally leaves. The color observed depends both on the structure of the predominant genin and on the conditions of the medium in which the anthocyanin colorants are present.

SUMMARY OF THE INVENTION

It has now unexpectedly and surprisingly been determined that certain flavylium salt compounds not substituted at position-3, but otherwise substituted with at least one hydroxyl or alkoxy radical, immediately impart to the skin, after having been topically applied thereon, an artificial coloration quite similar to that of a natural tan.

The present invention thus features novel cosmetic and/or dermatological compositions for imparting to the skin an artificial coloration closely resembling that of a natural tan, comprising, formulated into a cosmetically acceptable support (vehicle, diluent or carrier), at least one flavylium salt compound which is not substituted at position-3 thereof and which is otherwise substituted with at least one hydroxyl or alkoxy radical, said at least one flavylium salt being obtained synthetically or from a plant extract containing same, or, alternatively, from an enriched plant extract, in an amount which is effective for providing 30 minutes after application to a fair skin at a rate of 2 mg/cm$^2$, a darkening of the color of the skin characterized in the L*a*b* colorimetric measuring system by a ΔL* ranging from −0.5 to −20.

The present invention also features a regime/regimen for the artificial tanning/darkening of human skin to an extent that resembles a natural tan, by topically applying thereon, for such period of time as required to elicit the desired effect, at least one flavylium salt compound which is unsubstituted at position-3 thereof and which is otherwise substituted with at least one hydroxyl or alkoxy radical, whether obtained synthetically, from a plant extract, or from an enriched plant extract containing same.

DETAILED DESCRIPTION OF BEST MODE AND SPECIFIC/PREFERRED EMBODIMENTS OF THE INVENTION

More particulary according to the present invention, the subject compositions permit obtaining an artificial skin coloration approximately that of a natural tan in a very short space of time. Thus, an immediate coloration is obtained, which allows visualization of the application and consequently better homogeneity in the spreading of the composition onto the skin and, hence, of the resulting skin coloration. Furthermore, the artificial coloration obtained on the skin according to the invention is extremely close to that of a natural tan.

For the purposes of the present invention, by the expression "composition intended for artificially coloring the skin" is intended a formulation with a particular affinity for the skin which imparts to the skin a long-lasting coloration, which is non-covering (namely, which does not have a tendency to opacify the skin) and which is not removed either with water or with a solvent, and which withstands both rubbing and washing with a solution containing surfactants. Such a long-lasting coloration is thus distinguished from the superficial and transient coloration provided, for example, by a makeup product.

The compositions in accordance with the present invention permit obtaining, 30 minutes after application to a fair skin at a rate of 2 mg/cm$^2$, a darkening characterized in the (L*, a*, b*) colorimetric measuring system by a ΔL* ranging from −0.5 to −20. Preferably, ΔL* will range from −0.5 to −15.

The compositions of the present invention provide, 30 minutes after application to the skin at a rate of 2 mg/cm$^2$, a coloration on a fair skin defined in the (L*, a*, b*) calorimetric measuring system, by a ratio Δa*/Δb* ranging from 0.5 to 3 and even more particularly ranging from 0.8 to 2.

According to the present invention, by the term "fair skin" is intended an untanned skin whose colorimetric characteristics may be defined by its ITA angle as defined in the publication by A. Chardon et al. "Skin Color Typology and Suntanning Pathways" presented at the 16th IFSCC congress, Oct. 8–10, 1990, New York, and in *Int. J. Cosm. Sci.*, 13, 191–208 (1991). The fair skins as defined in this classification have an ITA° angle ranging from 35 to 55.

In the (L*, a*, b*) colorimetric measuring system:
L* represents the luminance or clarity, a* represents the red-green axis (−a*=green, +a*=red) and b* represents the yellow-blue axis (−b*=blue, +b*=yellow). Thus, a* and b* express the shade of the skin;
ΔL* reflects the darkening of the color: the more negative the ΔL*, the darker the color becomes, with:

Δ*L*\*=*L*\* uncolored skin−*L*\* colored skin;

The ratio Δa*/Δb* reflects the red/yellow balance and thus the shade, with:
Δa*=a* uncolored skin−a* colored skin
Δb*=b* uncolored skin−b* colored skin.

Among the flavylium salt compounds which are unsubstituted at position-3 in accordance with the invention, those which are preferred have the structural formula (I) below:

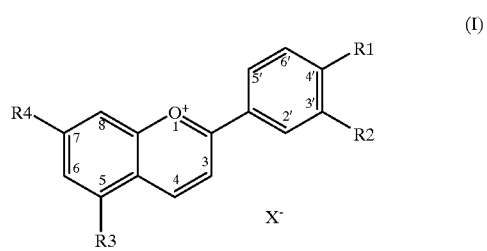

(I)

in which $R_1$ is an —OH group or a linear or branched, saturated or unsaturated $C_1$–$C_8$ alkoxy radical; $R_2$, $R_3$ and $R_4$, which may be identical or different, are each H or $R_1$, with the proviso that at least one of the radicals $R_1$ to $R_4$ is —OH; and X⁻ is an organic or inorganic anion and preferably a mineral acid derivative such as, for example, a halide, for example a bromide or chloride, or an organic acid derivative such as, for example, acetate, borate, citrate, tartrate, lactate, bisulfate, sulfate or phosphate.

The compounds of formula (I) that are particularly preferred according to the present invention are selected from among those, wherein formula (I), $R_1$ is —OH or —OCH$_3$.

Particularly exemplary thereof are the chlorides of the following compounds:
4',5,7-trihydroxyflavylium, commonly known as "apigeninidine chloride";
3',4',7-trihydroxyflavylium;
4'-hydroxyflavylium;
4',7-dihydroxyflavylium;
3',4'-dihydroxyflavylium;
3',4'-dihydroxy-7-methoxyflavylium;
3',4',5,7-tetrahydroxyflavylium;
3',4',5',5,7-pentahydroxyflavylium.

Among these compounds, apigeninidine chloride (4',5,7-trihydroxyflavylium chloride) and 3',4',7-trihydroxyflavylium chloride are even more particularly preferred.

In one particular embodiment of the invention, apigeninidine chloride is employed in the form of a plant extract, which is readily prepared by extraction, and isolated, from leaves of *Sorghum caudatum* according to the processes described in CN-1,064,284A and CN-1,035,512C or any other variants of these processes.

It may also be extracted from the stems, seeds or leaves of Sorghum bicolor, from the petals of *Gesneria fulgens*, and also from the species *Blechum procerum* and Sorghum in combination with *Colletotrichum graminicola*.

One particularly preferred embodiment of the invention entails use of an extract from the leaves of Sorghum bicolor obtained via by an aqueous/alcoholic extraction in acidic medium at an extraction temperature ranging from 30° to 40° C. with a ratio of the volume of solvent to the volume of Sorghum bicolor leaves ranging from 10 to 30. Said Sorghum plant extract has an approximate titer of from 0.05% to 50% by weight of apigeninidine chloride.

The flavylium salt compounds of this invention which are unsubstituted at position-3 thereof and which are substituted with at least one hydroxyl or alkoxy radical may be readily and inexpensively obtained by synthesis, in particular by the well-known method of R. Robinson and D. D. Pratt, *J. Chem. Soc.*, 745 (1923). Such method entails condensing an ortho-hydroxy-benzaldehyde or substitution derivatives thereof with an acetophenone or substitution derivatives thereof, to give, by selecting the substituents, the desired compounds of formula (I).

With apigeninidine chloride (4',5,7-trihydroxyflavylium chloride) as an example, the synthetic scheme (i) may be as follows:

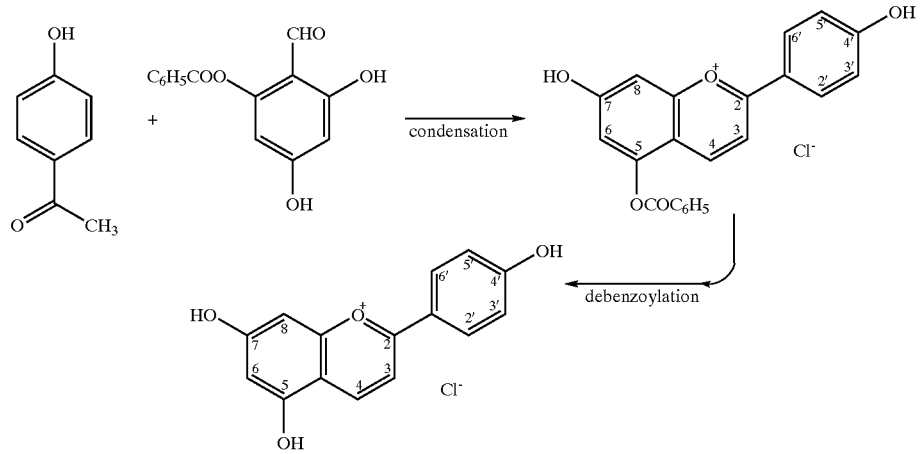

With 3',4',7-trihydroxyflavylium chloride as an example, the synthetic scheme (ii) may be as follows:

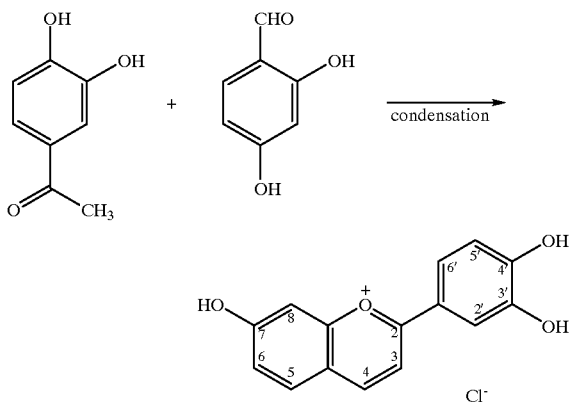

Various synthetic mechanisms well known to the prior art, produce apigeninidine.

One method includes, for example, in a first step, preparing trimethylapigeninidine by condensing commercially available 4,6-dimethoxy-2-hydroxybenzaldehyde with commercially available 4-methoxyacetophenone in anhydrous ether medium at 0° C., and saturation with anhydrous HCl, to yield, after filtration, an orange/red precipitate of trimethylapigeninidine. In a second step, the trimethylapigeninidine obtained in the first step is hydrolyzed to apigeninidine chloride, the reaction being carried out in a medium of HI and phenol and AgCl dissolved in methanol. Such a synthetic method is disclosed by R. Robinson and A. Robertson in *J. Chem. Soc.,* 1951 (1926) and 2196 (1927).

Another technique entails condensing 2,4,6-trihydroxybenzaldehyde with 4-hydroxyacetophenone at 0° C. in an anhydrous solvent medium, for example ethyl acetate, and saturation with anhydrous HCl, to provide apigeninidine chloride. Such a method is described by R. Robinson and A. Robertson in *J. Chem. Soc.,* 1528 (1928).

Another technique for preparing apigeninidine chloride entails reducing a flavone, naringenin, or its triacetyl derivative, with NaBH$_4$, and then oxidizing the product obtained with chloranil (tetrachloro-1,4-benzoquinone). Such method is described by J. G. Sweeny and G. A. Iacobucci in the review *Tetrahedron,* 33, 2923–2927 (1977).

The process more particularly preferred according to the present invention comprises condensing 2,4-dihydroxy-6-benzoyloxybenzaldehyde with 4-hydroxyacetophenone at 0° C. in anhydrous ethyl acetate medium, saturating with anhydrous HCl and then debenzoylating the product obtained with sodium hydroxide, to give apigeninidine chloride in high yield, according to scheme (i) described above. This method is described by R. Robinson and J. C. Bell in *J. Chem. Soc.,* 813 (1934).

The concentration of the flavylium salt compound according to the present invention preferably ranges from about 0.0001% to 10% and even more preferably from 0.001% to 5% by weight relative to the total weight of the composition.

The compositions according to the present invention may also comprise conventional cosmetic adjuvants and additives, selected, in particular, from among the fatty substances, organic solvents, ionic or nonionic thickeners, softeners, antioxidants, free-radical scavengers, opacifiers, stabilizers, emollients, silicones, α-hydroxy acids, insect repellents, antifoaming agents, moisturizers, vitamins, fragrances, preservatives, surfactants, fillers, polymers, propellants, acidifying or basifying agents, colorants or any other ingredient usually included in cosmetics and/or dermatology, in particular for producing antisun/sunscreen compositions in the form of emulsions.

The fatty substances may be an oil or a wax or mixtures thereof. By the term "oil" is intended a compound which is liquid at room temperature. By the term "wax" is intended a compound which is solid or substantially solid at room temperature and whose melting point is generally greater than 35° C.

Exemplary oils include mineral oils (paraffin); plant oils (sweet almond oil, macadamia oil, blackcurrent seed oil, jojoba oil); synthetic oils such as perhydrosqualene, fatty alcohols, fatty acids or fatty esters (such as the $C_{12}$–$C_{15}$ alkyl benzoate marketed under the trademark "Finsolv TN" by Finetex, octyl palmitate, isopropyl lanolate, triglycerides including those of capric/caprylic acid), oxyethylenated or oxypropylenated fatty esters and ethers; silicone oils (cyclomethicone, polydimethylsiloxanes or PDMSs) or fluoro oils, and polyalkylenes.

Exemplary waxy compounds include paraffin, carnauba wax, beeswax and hydrogenated castor oil.

And exemplary organic solvents include the lower alcohols and polyols.

According to one particularly preferred embodiment, the compositions of the invention contain at least 5% by weight, relative to the total weight of the composition, of one or more polyhydroxylated solvents. These solvents may be selected from among glycols and glycol ethers, for example ethylene glycol, propylene glycol, butylene glycol, dipropylene glycol or diethylene glycol. More preferably, the compositions according to the invention contain a mixture of at least three different polyhydroxylated solvents and even more preferably a mixture of propylene glycol, butylene glycol and dipropylene glycol.

The thickeners are advantageously selected, in particular, from among crosslinked polyacrylic acids and modified or unmodified guar gums and celluloses, such as hydroxyprolyl guar gum, methylhydroxyethylcellulose and hydroxypropylmethylcellulose.

One skilled in the art will of course take care to select the optional additional compound(s) indicated above and/or the amounts thereof such that the advantageous properties intrinsically associated with the flavylium salt compounds in accordance with the invention are not, or are not substantially, adversely affected by the addition(s) envisaged.

The compositions according to the invention may be formulated according to techniques that are well known to those skilled in this art, in particular those for the formulation of oil-in-water or water-in-oil emulsions.

The subject compositions may, in particular, be formulated in the form of a simple or complex (O/W, W/O, O/W/O or W/O/W) emulsion such as a cream or a milk, or in the form of a gel or a cream-gel, in the form of a lotion, a powder or a solid tube, or stick, and may optionally be packaged as an aerosol and may be in the form of a mousse or spray.

The compositions according to the invention are preferably in the form of an oil-in-water (O/W) or water-in-oil (W/O) emulsion.

When the composition is an emulsion, the aqueous phase of this emulsion may comprise a nonionic vesicular dispersion prepared according to known processes (Bangham, Standish and Watkins, *J. Mol. Biol.,* 13, 238 (1965), FR-2,315,991 and FR-2,416,008).

In order to further illustrate the present invention and the advantages thereof, the following specific examples are given, it being understood that same are intended only as illustrative and in nowise limitative.

EXAMPLE 1

An extract of Sorghum bicolor with a titer of 20%–30% of apigeninidine chloride was prepared according to the following preparative technique:

An extract from the leaves of Sorghum bicolor was obtained by aqueous/alcoholic (95° ethanol) extraction in acidic medium (0.2% HCl) at an extraction temperature of 35° C. with a ratio of the volume of solvent to the mass of Sorghum bicolor leaves of 15. The Sorghum plant extract was oven-dried for 24 hours at 40° C. and screened at 200 μm.

The yield for this extraction was 22.42% colorant matter.

The titer for the extract thus obtained was 21% by weight of apigeninidine chloride.

This example indicates, in a first stage, the intensity of the coloration obtained with an extract of Sorghum bicolor in accordance with the present invention, and also the speed with which this coloration develops compared with a composition containing DHA as skin-coloring agent.

This example also indicates, in a second stage, that the coloration obtained with an extract of Sorghum bicolor in accordance with the present invention is close to that of a natural tan on the skin.

EXAMPLE 2

The following compositions were formulated (the amounts are expressed as percentages by weight relative to the total weight of the composition):

Composition A (not according to the invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean oil | 0.1 g |
| Dihydroxyacetone (DHA) | 4 g |
| Sodium chloride | 2 g |
| Propylene glycol | 23 g |
| Butylene glycol | 5 g |
| Dipropylene glycol | 10 g |
| Demineralized water | 32,649 g |
| Trisodium citrate | 0.542 g |
| Citric acid | 0.209 g |

Composition B (invention):

| | |
|---|---|
| Polydimethyl/methyl siloxane POE/POP (396/4) (EO/PO 18/18) at 10% D5 | 10 g |
| Cyclopentadimethylsiloxane | 12.5 g |
| Mixture of natural tocopherols/soybean | 0.1 g |
| Demineralized water | 36.159 g |
| Sodium chloride | 2 g |
| Propylene glycol | 23 g |
| Butylene glycol | 5 g |
| Dipropylene glycol | 10 g |
| Extract of Sorghum bicolor as prepared above | 0.5 g |
| Trisodium citrate | 0.535 g |
| Citric acid | 0.206 g |

Evaluation Protocol:

Compositions A and B were applied onto the skin at a rate of 2 mg/cm$^2$ to an area of 7×4.5 cm$^2$ delimited on the back of six volunteers whose skin color, characterized by the ITA angle, ranged from 35 to 55.

The five series of colorimetric measurements below were carried out using a Minolta CR-300 calorimeter:

(1) before applying the composition,
(2) 30 minutes after the application,
(3) 2 hours after application,
(4) 4 hours after application,
(5) 5 hours after application.

The results are expressed in the (L*, a*, b*) system in which L* represents the luminance, a* represents the red-green axis (−a*=green, +a*=red) and b* represents the yellow-blue axis (−b*=blue, +b*=yellow). Thus, a* and b* express the shade of the skin.

To evaluate the intensity of the coloration, the important value is the ΔL* which reflects the darkening of the color: the more negative the ΔL*, the more the color is darkened, with:

ΔL*=L* uncolored skin−L* colored skin

For the shade of the coloration obtained, the important value is the ratio Δa*/Δb* which reflects the red/yellow balance and thus the shade, with:

Δa*=a* uncolored skin−a* colored skin
Δb*=b* uncolored skin−b* colored skin

The results obtained are reported in the Table below:

TABLE

| | Composition A (comparative) ΔL* | Composition B (invention) ΔL* | Composition B (invention) Δa*/Δb* |
|---|---|---|---|
| 30 minutes | −0.4 | −8.2 | 1.6 |
| 2 hours | −1.1 | −7 | 1.4 |
| 4 hours | −2.5 | −6.7 | 1.6 |
| 5 hours | −2.6 | −6.9 | 1.7 |

It thus was found that 30 minutes after application, composition A, which contained DHA as the self-tanning agent, imparted to the skin only a very faint coloration, since the DHA had not yet had the time required to function (ΔL*=−0.4). On the other hand, composition B according to the invention had already provided the skin with a significant coloration (ΔL*=−8.2).

Composition A containing DHA did not impart, after 30 minutes, a darkening comparable to that of composition B, which furthermore had a constant coloration shade for 5 hours.

Composition B provided a coloration on the skin which was close to that of a natural tan and which was constant over time.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition for artificially tanning/darkening human skin to such extent as to resemble a natural tan, comprising a thus effective amount of at least one flavylium salt compound formulated into a topically applicable, cosmetically/dermatologically acceptable vehicle, diluent or carrier therefor, said at least one flavylium salt compound being unsubstituted at position-3 thereof, but otherwise substituted with at least one hydroxyl group or alkoxy radical.

2. A topically applicable cosmetic/dermatological compositions for artificially tanning/darkening human skin to such extent as to resemble a natural tan, comprising an amount of at least one flavylium salt compound effective to impart a skin coloration, within about 30 minutes after topical application onto a fair skin, at a rate of 2 mg/cm$^2$, characterized by a $\Delta L^*$ ranging from −0.5 to −20 in the L*a*b* colorimetric measuring system, said at least one flavylium salt compound being formulated into a topically applicable, cosmetically/dermatologically acceptable vehicle, diluent or carrier therefor, and said at least one flavylium salt compound being unsubstituted at position-3 thereof, but otherwise substituted with at least one hydroxyl group or alkoxy radical.

3. The topically applicable cosmetic/dermatological composition as defined by claim 2, said $\Delta L^*$ ranging from −0.5 to −15.

4. The topically applicable cosmetic/dermatological composition as defined by claim 2, comprising an amount of said at least one flavylium salt compound effective to impart a skin coloration also characterized by a ratio $\Delta a^*/\Delta b^*$ ranging from 0.5 to 3.

5. The topically applicable cosmetic/dermatological composition as defined by claim 4, said ratio $\Delta a^*/\Delta 5^*$ ranging from 0.8 to 12.

6. The topically applicable cosmetic/dermatological composition as defined by claims 1 or 2, said at least one flavylium salt compound having the structural formula (I):

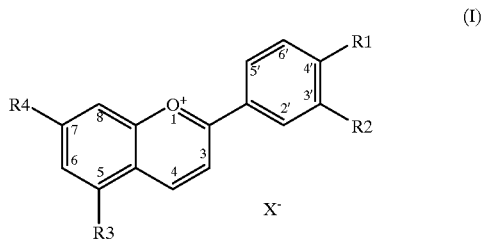

in which $R_1$ is an —OH group or linear or branched, saturated or unsaturated $C_1$–$C_8$ alkoxy radical; $R_2$, $R_3$ and $R_4$, which may be identical or different, are each H or $R_1$, with the proviso that at least one of the radicals $R_1$ to $R_4$ is OH; and X$^-$ is an organic or mineral anion.

7. The topically applicable cosmetic/dermatological composition as defined by claim 6, wherein formula (I), X$^-$ is an halide or anion of an organic acid.

8. The topically applicable cosmetic/dermatological composition as defined by claim 6, wherein formula (I), $R_1$ is —OH or —OCH$_3$.

9. The topically applicable cosmetic/dermatological composition as defined by claim 6, said at least one flavylium salt compound having the structural formula (I) comprising the chloride of 4',5,7-trihydroxyflavylium (apigeninidine chloride), 3',4',7-trihydroxyflavylium, 4'-hydroxyflavylium, 4',7-dihydroxyflavylium, 3',4'-dihydroxyflavylium, 3',4'-dihydroxy-7-methoxyflavylium, 3',4',5,7-tetrahydroxyflavylium, or 3',4',5',5,7-pentahydroxyflavylium.

10. The topically applicable cosmetic/dermatological composition as defined by claim 9, said at least one flavylium salt compound comprising pure 4',5,7-trihydroxyflavylium chloride.

11. The topically applicable cosmetic/dermatological composition as defined by claim 9, said at least one flavylium salt compound comprising a 4',5,7-trihydroxyflavylium chloride plant extract.

12. The topically applicable cosmetic/dermatological composition as defined by claims 1 or 2, said at least one flavylium salt compound comprising a synthetic species, or a plant or enriched plant extract thereof.

13. The topically applicable cosmetic/dermatological composition as defined by claim 12, said at least one flavylium salt compound comprising a plant extract obtained from leaves of *Sorghum caudatum*; from stems, seeds or leaves of Sorghum bicolor; from the petals of *Gesneria fulgens*, or from the species *Blechum procerum* and Sorghum in combination with *Colletotrichum graminicola*.

14. The topically applicable cosmetic/dermatological composition as defined by claim 13, said at least one flavylium salt compound comprising a plant extract of Sorghum bicolor obtained via acidic aqueous/alcoholic extraction at an extraction temperature ranging from 30° C. to 40° C. with a ratio of the volume of solvent to the mass of Sorghum bicolor leaves ranging from 10 to 30.

15. The topically applicable cosmetic/dermatological composition as defined by claim 13, said at least one flavylium salt compound comprising a plant extract from Sorghum bicolor, said extract having a titer of from 0.05% to 50% by weight of 4',5,7-trihydroxyflavylium chloride.

16. The topically applicable cosmetic/dermatological composition as defined by claims 1 or 2, comprising from 0.0001% to 10% by weight of said at least one flavylium salt compound.

17. The topically applicable cosmetic/dermatological composition as defined by claim 16, comprising from 0.001% to 5% by weight of said at least one flavylium salt compound.

18. The topically applicable cosmetic/dermatological composition as defined by claims 1 or 2, comprising at least 5% by weight of at least one polyhydroxylated solvent.

19. The topically applicable cosmetic/dermatological composition as defined by claim 18, said at least one polyhydroxylated solvent comprising a glycol or glycol ether.

20. The topically applicable cosmetic/dermatological composition as defined by claim 18, said at least one polyhydroxylated solvent comprising ethylene glycol, propylene glycol, butylene glycol, dipropylene glycol, diethylene glycol, or mixture thereof.

21. The topically applicable cosmetic/dermatological composition as defined by claim 18, comprising a mixture of at least three different polyhydroxylated solvents.

22. The topically applicable cosmetic/dermatological composition as defined by claim 21, comprising a mixture of propylene glycol, butylene glycol and dipropylene glycol.

23. The topically applicable cosmetic/dermatological composition as defined by claims 1 or 2, formulated as an emulsion, cream, milk, gel, cream-gel, lotion, powder, solid, aerosol, mousse, or spray.

24. A regime or regimen for artificially tanning/darkening human skin to such extent as to resemble a natural tan, comprising topically applying thereon, for such period of time as required to elicit the desired response, a cosmetic/dermatological composition which comprises a thus effective amount of at least one flavylium salt compound formulated into a topically applicable, cosmetically/dermatologically acceptable vehicle, diluent or carrier therefor, said at least one flavylium salt compound being unsubstituted at position-3 thereof, but otherwise substituted with at least one hydroxyl group or alkoxy radical.

25. A regime or regimen for artificially tanning/darkening human skin to such extent as to resemble a natural tan, comprising topically applying thereon, for such period of time as required to elicit the desired response, a cosmetic/dermatological composition which comprises an amount of at least one flavylium salt compound effective to impart a skin coloration, within about 30 minutes after topical application onto a fair skin, at a rate of 2 mg/cm$^2$, characterized by a $\Delta L^*$ ranging from $-0.5$ to $-20$ in the $L^*a^*b^*$ colorimetric measuring system, said at least one flavylium salt compound being formulated into a topically applicable, cosmetically/dermatologically acceptable vehicle, diluent or carrier therefor, and said at least one flavylium salt compound being unsubstituted at position-3 thereof, but otherwise substituted with at least one hydroxyl group or alkoxy radical.

26. The regime or regimen as defined by claims 24 or 25, said at least one flavylium salt compound having the structural formula (I):

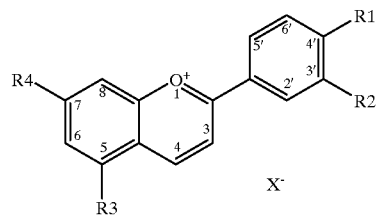

in which $R_1$ is an —OH group or linear or branched, saturated or unsaturated $C_1$–$C_8$ alkoxy radical; $R_2$, $R_3$ and $R_4$, which may be identical or different, are each H or $R_1$, with the proviso that at least one of the radicals $R_1$ to $R_4$ is OH; and $X^-$ is an organic or mineral anion.

* * * * *

UNITED STATES PATENT AND TRADEMARK OFFICE
CERTIFICATE OF CORRECTION

PATENT NO. : 6,558,655 B2
DATED : May 6, 2003
INVENTOR(S) : Didier Candau et al.

It is certified that error appears in the above-identified patent and that said Letters Patent is hereby corrected as shown below:

Column 8,
Lines 64-65, "compositions" should read -- composition --.

Column 9,
Line 20, "Δa*/Δ5*" should read -- Δa*/Δb* --.
Between lines 27-35, in the structure for formula (I),

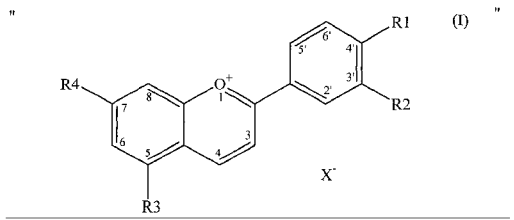

should read

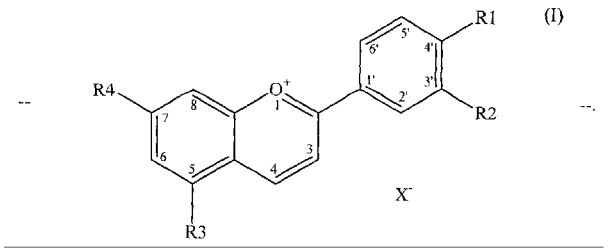

Column 9,
Lines 46-47, "an halide" should read -- a halide --.

UNITED STATES PATENT AND TRADEMARK OFFICE
CERTIFICATE OF CORRECTION

PATENT NO. : 6,558,655 B2
DATED : May 6, 2003
INVENTOR(S) : Didier Candau et al.

It is certified that error appears in the above-identified patent and that said Letters Patent is hereby corrected as shown below:

Column 12,
Top of column, structure for formula (I),

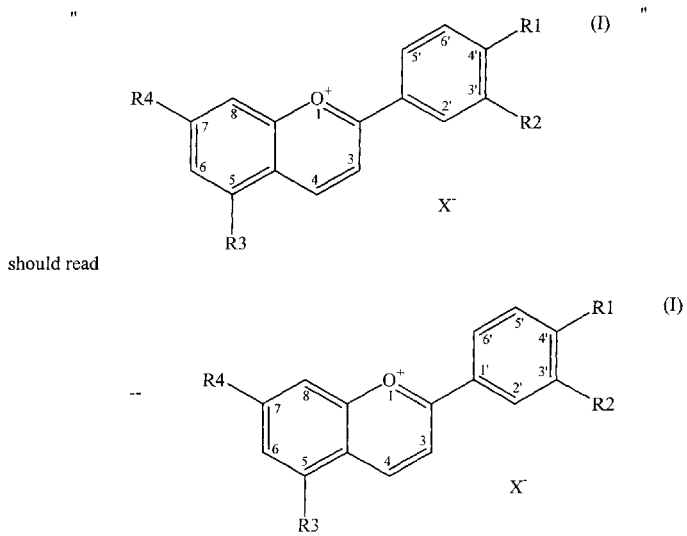

should read

Signed and Sealed this

Fourteenth Day of September, 2004

JON W. DUDAS
*Director of the United States Patent and Trademark Office*